(12) United States Patent
Klein et al.

(10) Patent No.: US 10,930,389 B2
(45) Date of Patent: Feb. 23, 2021

(54) SYSTEMS AND METHODS FOR THE CLASSIFICATION AND INDEXING OF CONTRACT DOCUMENTATION

(71) Applicant: Change Healthcare Holdings, LLC, Nashville, TN (US)

(72) Inventors: Julian Oliver Klein, Phoenixville, PA (US); Shiradwade Sateesh Krishna, Chester Springs, PA (US); Xiaoming Zhang, Portland, OR (US); Michael Anthony Zupper, Allentown, PA (US); Amit Arun Dalvi, Chester Springs, PA (US)

(73) Assignee: Change Healthcare Holdings, LLC, Nashville, TN (US)

(*) Notice: Subject to any disclaimer, the term of this patent is extended or adjusted under 35 U.S.C. 154(b) by 1297 days.

(21) Appl. No.: 15/001,973

(22) Filed: Jan. 20, 2016

(65) Prior Publication Data
US 2017/0206326 A1    Jul. 20, 2017

(51) Int. Cl.
*G16H 40/20* (2018.01)
*G06Q 50/18* (2012.01)
*G06Q 40/08* (2012.01)

(52) U.S. Cl.
CPC ............ *G16H 40/20* (2018.01); *G06Q 40/08* (2013.01); *G06Q 50/18* (2013.01)

(58) Field of Classification Search
None
See application file for complete search history.

(56) References Cited

U.S. PATENT DOCUMENTS

| 5,446,653 | A  | * | 8/1995 | Miller | G06F 17/243 |
|---|---|---|---|---|---|
|   |   |   |   |   | 705/4 |
| 6,873,992 | B1 | * | 3/2005 | Thomas | G06Q 10/10 |
| 2017/0011313 | A1 | * | 1/2017 | Pochert | G06F 3/0481 |

* cited by examiner

*Primary Examiner* — Devin C Hein
(74) *Attorney, Agent, or Firm* — Meunier Carlin & Curfman LLC

(57) ABSTRACT

A request for contract documentation is received from a provider computer. One or more classifier values associated with the request are compared to one or more values stored in one or more index cores. Based on the determination that a match exists, one or more contracting documents are retrieved from a contracts database, where the contracts database includes the updated format of each of the contracting documents. A contract template is generated including the one or more contracting documents. The contract template is compiled and communicated for signature and subsequent approval.

20 Claims, 5 Drawing Sheets

SYSTEMS AND METHODS FOR THE CLASSIFICATION AND INDEXING OF CONTRACT DOCUMENTATION

TECHNICAL FIELD

Aspects of the disclosure relate generally to generating healthcare plans, and more particularly, to systems and methods for the classification and indexing of contract templates based upon provider criteria and using the provider criteria to generate a provider agreement.

BACKGROUND

Administrative costs associated with healthcare plans for a provider are increasing exponentially as providers feel significant downward pressure in light of mandates associated with the Affordable Care Act. One area that a healthcare plans may have an opportunity to reduce administrative expenses may be in a provider contract management department. For example, generally 80% of all contracting for a healthcare plan are standard or non-negotiated contracts while 20% require a hand on negotiation. However, provider contract management departments are still putting a great deal of manual effort and intervention from a provider contract management department perspective into the 80%. This manual intervention represents unnecessary expense in that the resources of the provider contract management department perspective could be focused on more valuable tasks.

Furthermore, while many health plans utilize a standard contract template, the contracting process between the provider contract management department and the providers is still very much a manual process. However, the contract management solutions, such as the standard contract templates, are typically for general procurement and are not specific to the needs of a specific provider. Therefore, these procurement solutions do not include the attributes and capabilities needed to efficiently manage the generation of a healthcare provider plan specific to a provider.

BRIEF DESCRIPTION OF THE DRAWINGS

Reference will now be made to the accompanying drawings, which are not necessarily drawn to scale, and wherein.

DETAILED DESCRIPTION OF EXAMPLE EMBODIMENTS

Exemplary embodiments will now be described more fully hereinafter with reference to the accompanying drawings, in which example embodiments are shown. The concepts disclosed herein may, however, be embodied in many different forms and should not be construed as limited to the example embodiments set forth herein; rather, these embodiments are provided so that this disclosure will be thorough and complete, and will fully convey the scope of the concepts to those skilled in the art. Like numbers refer to like, but not necessarily the same or identical, elements throughout.

Example embodiments described herein include systems and methods that facilitate the classification and indexing of contract templates based upon provider criteria and using the provider criteria to generate a provider agreement. In one example, a search engine module may receive a provider agreement request. The search engine module may generate a contract template corresponding to provider information submitted in the provider agreement request. For example, a provider, such as a physician, office manager, etc., may submit a provider agreement request via a healthcare provider computer. The provider agreement request may include information specific to that provider, for example, a provider address, a provider phone number, a provider specialty, a provider line of business, etc. A service provider computer may use the provider information to generate a contract template specific to the provider information.

In one example embodiment, the service provider computer may utilize a search engine module to search an index of keys distributed across multiple core files to generate the contract template. In one example, a key value may correspond to one or more documents used by the search provider computer to generate the contract template. The key value identified during a query of the one or more core files may be used to access a corresponding contract entity (e.g., a document, a contract, a contract template, etc.) in a database, such as a contract manager database. If one or more contract entities are found, the contract entities may be compiled, generating a contract template. The contract template may, in certain embodiments, be populated using the information submitted by the provider in the provider agreement request. A pre-populated contract template may be communicated to the provider via the healthcare provider computer for signature.

System Overview

Figure 1:
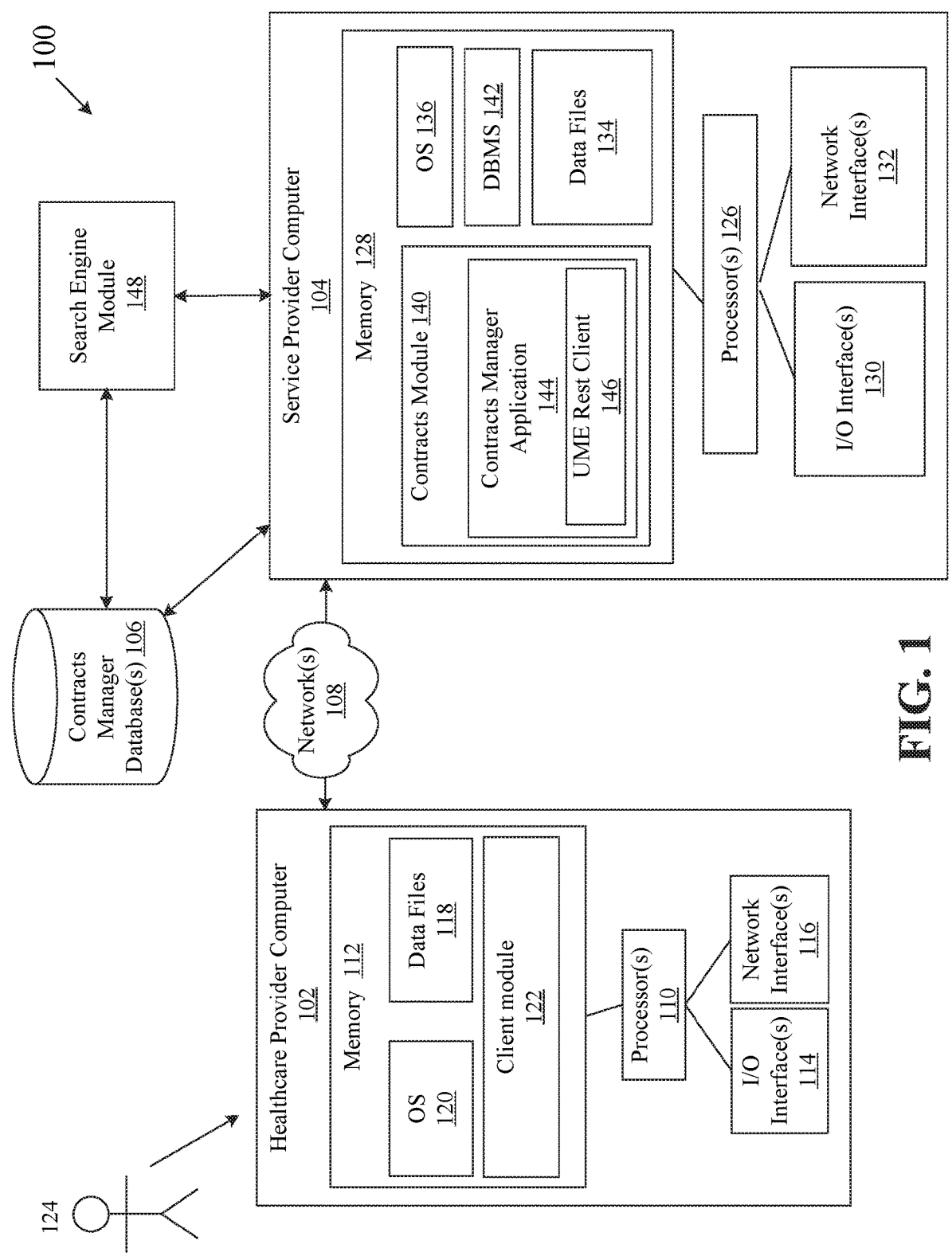
FIG. 1 illustrates an example overview of a system that facilitates the classification and indexing of contract templates based upon provider criteria and using the provider criteria to generate a provider agreement according to one exemplary embodiment.

FIG. 1 illustrates an example system 100 supporting the classification and indexing of contract documentation and templates for identification based upon provider criteria utilized to automate the generation of a provider agreement according to one example embodiment. The exemplary system 100 facilitates the generation of a provider agreement based on the identification of provider criteria provided by a healthcare provider as part of a provider agreement request and will now be described illustratively with respect to FIG. 1. As shown in FIG. 1, the system 100 may include at least one healthcare provider computer 102 and at least one service provider computer 104.

As desired, each of the healthcare provider computer 102, service provider computer 104, and/or search engine module 148 may include one or more processing devices that may be configured for accessing and reading associated computer-readable media having stored thereon data and/or computer-executable instructions for implementing the various methods disclosed in the exemplary embodiments discussed here.

Additionally, in certain exemplary embodiments, the service provider computer 104 and/or the search engine module 148 may be in communication with one or more data storage devices, such as a contract manager database 106. The contract manager database 106 may receive, store, and provide, as needed, contract templates from the service provider computer 104 and/or the search engine module 148. In certain exemplary embodiments, the contract manager database 106 may also include, without limitation, one or more classifier values associated with a contract template. The one or more classifier values may be used by the search engine module 148 during an automated generation of a provider agreement and will be discussed in more detail herein. Alternatively, the data storage function may be included in the service provider computer 104 and/or the search engine module 148 themselves, such as in the memory 128.

Generally, network devices and systems, including one or more of the healthcare provider computer 102, the service provider computer 104, and the search engine module 148 may include or otherwise be associated with suitable hardware and/or software for transmitting and receiving data and/or computer-executable instructions over one or more communications links or networks. These network devices and systems may also include any number of processors for processing data and executing computer-executable instructions, as well as other internal and peripheral components that are well known in the art. Further, these network devices and systems may include or be in communication with any number of suitable memory devices operable to store data and/or computer-executable instructions. By executing computer-executable instructions, each of the network devices forms a special purpose computer or particular machine. As used herein, the term "computer-readable medium" describes any form of suitable memory or memory device.

As shown in FIG. 1, the healthcare provider computer 102, the service provider computer 104, the search engine module 148, and the contracts manager database 106 may be in communication with each other via one or more networks, such as network 108, which as described below can include one or more separate or shared private and public networks, including the Internet. Each of these components, the healthcare provider computer 102, the service provider computer 104, the search engine module 148, the contracts manager database 106, and the network 108 will now be discussed in further detail.

Each healthcare provider computer 102 may be associated with (e.g., located within and/or providing computing services for) a healthcare provider, such as, for example, a physician's office, hospital, clinic, etc. While the exemplary healthcare provider computer 102 will be described as within or part of a physician's office or a physician practice management system with regards to FIGS. 1-5, this is for example only and is not intended to be limiting in any manner. Each healthcare provider computer 102 may be any suitable processor-driven device that facilitates the processing of a provider agreement request made by a provider and the communication of the information associated with the provider agreement request to the service provider computer 104, such as a server computer, a mainframe computer, one or more networked computers, a desktop computer, a personal computer, a digital assistant, a personal digital assistant, a digital tablet, an Internet appliance, an application-specific circuit, a microcontroller, a minicomputer, or any other processor-based device. The execution of the computer-implemented instructions by the healthcare provider computer 102 forms a special-purpose computer or other particular machine that is operable to facilitate the processing of provider agreement requests made by a provider and the communication of information associated with provider agreement requests to a service provider computer 104. Additionally, in certain example embodiments, the operations and/or control of each healthcare provider computer 102 may be distributed amongst several processing components.

In addition to having one or more processors 110, each healthcare provider computer 102 may include one or more memory devices 112, one or more input/output ("I/O") interfaces 114, and one or more network interfaces 116. The memory devices 112 may be any suitable memory device, for example, caches, read-only memory devices, random access memory devices, magnetic storage devices, removable storage devices, etc. The memory devices 112 may store data, executable instructions, and/or various program modules utilized by the healthcare provider computer 102, for example, the data files 118, an operating system ("OS") 120, and/or the client module 122, respectively. The data files 118 may include any suitable data that facilitates the receipt, generation and/or processing of provider agreement requests that are communicated to the service provider computer 104. For example, data files 118 may include, for example, information utilized by the service provider computer 104 to generate a provider agreement. For example, the data files 118 may include, without limitation, provider name(s), physical office location information, billing and service(s) information (e.g., address, phone number, etc.), tax identification numbers (TIN), provider ID or other identifier (e.g., NPI code), and the like. The OS 120 may be any suitable software module that controls the general operation of the healthcare provider computer 102. The OS may also facilitate the execution of other software modules by the one or more processors 110 and may be any currently existing or future-developed operating system including, but not limited to, Microsoft Windows®, Apple OSX™, Linux, Unix, or a mainframe operating system.

The client module 122 may be an Internet browser or other suitable software, including a dedicated program, for interacting with the service provider computer 104. For example, a user 124 may utilize the client module 122 in preparing and transmitting a provider agreement request. More specifically, the user 124 may access, for example, one or more applications, such as contracts manager application 144. As used herein, an application may refer generally to an application that is accessed over a network, or more specifically, to an application that may be coded in a browser-supported language and/or a browser rendered language, and which may require a web browser or other program to render the application executable. The contracts manager application 144 may include web pages(s) that include web form(s) that comprise one or more data fields for inputting data. The healthcare provider computer 102 may be configured to run one or more web browser applications for loading, viewing, and manipulating the web page(s) which form at least part of the contracts manager application(s). Each of the data field(s) provided in a web form may have one or more data types associated therewith that specify type(s) of input accepted for that field. Exemplary data types include but are not limited to, an integer data type, a Boolean data type, an alphanumeric character, an American Standard Code for Information Interchange (ASCII) character, a character string (e.g., a sequence of alphanumeric characters, a sequence of ASCII characters, etc.), enumerated types, derived data types, such as for example, lists, arrays, trees, and so forth, or any combinations thereof. Exemplary data types further include, but are not limited to, data types supported in number, street address, city, state, provider type, practice area, or the like. The data type(s) associated with a particular field in a web form may dictate type(s) of input accepted for that field. As a non-limiting example, acceptable inputs for an address field may include an alphanumeric character string or a string of ASCII characters. As another non-limiting example, an acceptable input for a telephone number data field may include a string of characters of a predetermined length. More specifically, character strings of a predetermined length that include only integers may be accepted.

In one example, the data input into each of one or more fields may include information utilized by the system 100 to identify an appropriate contract temple for the respective provider. For example, the one or more fields may correspond to one or more classifiers, for example, without limitation, an agreement type classifier, a region classifier, a line of business classifier (e.g., Medicare, Preferred Provider Organization ("PPO"), health maintenance organization ("HMO"), etc.), a provider type classifier, a provider sub-type classifier, a network classifier, and/or a business entity classifier. The use of the one or more classifiers to identify the appropriate contract template will be discussed in more detail herein.

The one or more I/O interfaces 114 may facilitate communication between the healthcare provider computer 102 and one or more input/output devices, for example, one or more interface devices, such as, a display, a keypad, keyboard, control panel, touch screen display, remote control, mouse, microphone, etc. that facilitate user interaction with the healthcare provider computer 102. For example, the one or more I/O interfaces 114 may facilitate entry of information associated with a provider agreement request by a user 124 of a healthcare provider computer 102, such as a physician, a nurse, an employee, a hospital, or other similar healthcare provider. The one or more network interfaces 116 may facilitate connection of the healthcare provider computer 102 to one or more suitable networks, for example, the network 108 illustrated in FIG. 1. In this regard, the healthcare provider computer 102 may receive and/or communicate information to other network components of the system 100, such as the service provider computer 104.

With continued reference to FIG. 1, the service provider computer 104 may include, but is not limited to, any suitable processor-driven device that is configured for receiving, processing, and fulfilling requests from the healthcare provider computer 102 and/or the search engine module 148 relating to provider agreement requests and/or other activities. In certain embodiments, the service provider computer 104 may include a suitable host server, host module, or other software that facilitates the receipt of a provider agreement request from the healthcare provider computer 102. Any number of healthcare provider computers 102 may be in communication with the service provider computer 104 via the network 108 for example, as desired in various embodiments.

The service provider computer 104 may include any number of special purpose computers or other particular machines, application-specific circuits, microcontrollers, personal computers, minicomputers, mainframe computer, servers, networked computers, and/or other processor-driven devices. In certain embodiments, the operations of the service provider computer 104 may be controlled by computer-executed or computer-implemented instructions that are executed by one or more processors 126 associated with the service provider computer 104 to form a special purpose computer or other particular machine that is operable to facilitate the receipt, routing, and/or processing of provider agreement requests. The one or more processors 126 that control the operations of the service provider computer 104 may be incorporated into the service provider computer 104 and/or in communication with the service provider computer 104 via one or more suitable networks. In certain exemplary embodiments, the operations and/or control of the service provider computer 104 may be distributed amongst several processing components.

Similar to the healthcare provider computer 102 described above, the service provider computer 104 may include one or more processors 126, one or more memory devices 128, one or more input/output ("I/O") interfaces 130, and one or more network interfaces 132. The one or more memory devices 128 may be any suitable memory devices, for example, caches, read only memory devices, random access memory devices, magnetic storage devices, removable memory devices, etc. The one or more memory devices 128 may store data, executable instructions, and/or various program modules utilized by the service provider computer 104, for example, data files 134, an operating system ("OS") 136, a host module 138, a contracts manager module 140, and a database management system ("DBMS") 142 to facilitate management of data files 134 and other data stored in the memory devices 128. The OS 136 may be a suitable software module that controls the general operation of the service provider computer 104 and/or facilitates the execution of other software modules. The OS 136 may be any currently existing or future-developed operating system including, but is not limited to, Microsoft Windows®, Apple OSX™, Linux, Unix, or a mainframe operating system.

The contracts manager module 140 may include, without limitation, a contracts manager application 144 and a Unified Metadata Engine (UME) REST client 146. The UME REST client 146 may be in communication with the search engine module 148. The search engine module 146 may identify an appropriate standard contract template for a respective provider using the classifier information received in a provider agreement request. For example, the search engine module 148 may receive the classifier information from the healthcare provider computer 102 and identify the corresponding standard contract template for the respective provider. More specifically, the search engine module 148 may utilize classifier information, such as, without limitation, agreement type, region, line of business, provider type, provider sub-type, network, business entity, etc., to identify and return to the healthcare provider computer 102 the contract template corresponding to the classifier information. The search engine module 148 will be discussed herein, for example, in FIG. 2.

The service provider computer 104 may include additional program modules for performing other processing methods described herein. Those of ordinary skill in the art will appreciate that the service provider computer 104 may include alternate and/or additional components, hardware or software without departing from exemplary embodiments of the disclosure.

With continued reference to the service provider computer 102, the one or more I/O interfaces 130 may facilitate communication between the service provider computer 104 and one or more input/output devices, for example, one or more user interface devices, such as a display, keypad, keyboard, mouse, control panel, touch screen display, remote control, microphone, etc. that facilitates user interaction with the service provider computer 104. The one or more network interfaces 132 may facilitate connection of the service provider computer 104 to one or more suitable networks, for example, the network 108 illustrated in FIG. 1. In this regard, the service provider computer 104 may communicate with other components of the system 100.

The contracts manager database 106 may include one or more contract entities, which may include, without limitation, one or more documents, templates, contracts, and/or provider entity data. The contracts manager database 106 may also, in certain embodiments, include one or more classifier values. In one example embodiment, the one or more classifier values correspond to one or more of the documents, templates, contracts, and/or provider entity data. In yet another example, the classifier value may correspond to a field within a document, template, contract, and or provider data. As described herein, the classifier values may be used to compile a contract template specific to user input, such as user 124.

Those of ordinary sill in the art will appreciate that the system 100 shown in and described with respect to FIG. 1 is provided by way of example only. Numerous other operating environments, system architectures, and device configurations are possible. Other system embodiments can include fewer or greater numbers of components and may incorporate some or all of the functionality described with respect to the system components shown in FIG. 1. Accordingly, the exemplary embodiments described herein should not be construed as being limited to any particular operating environment, system architecture, or device configuration.

Figure 2:
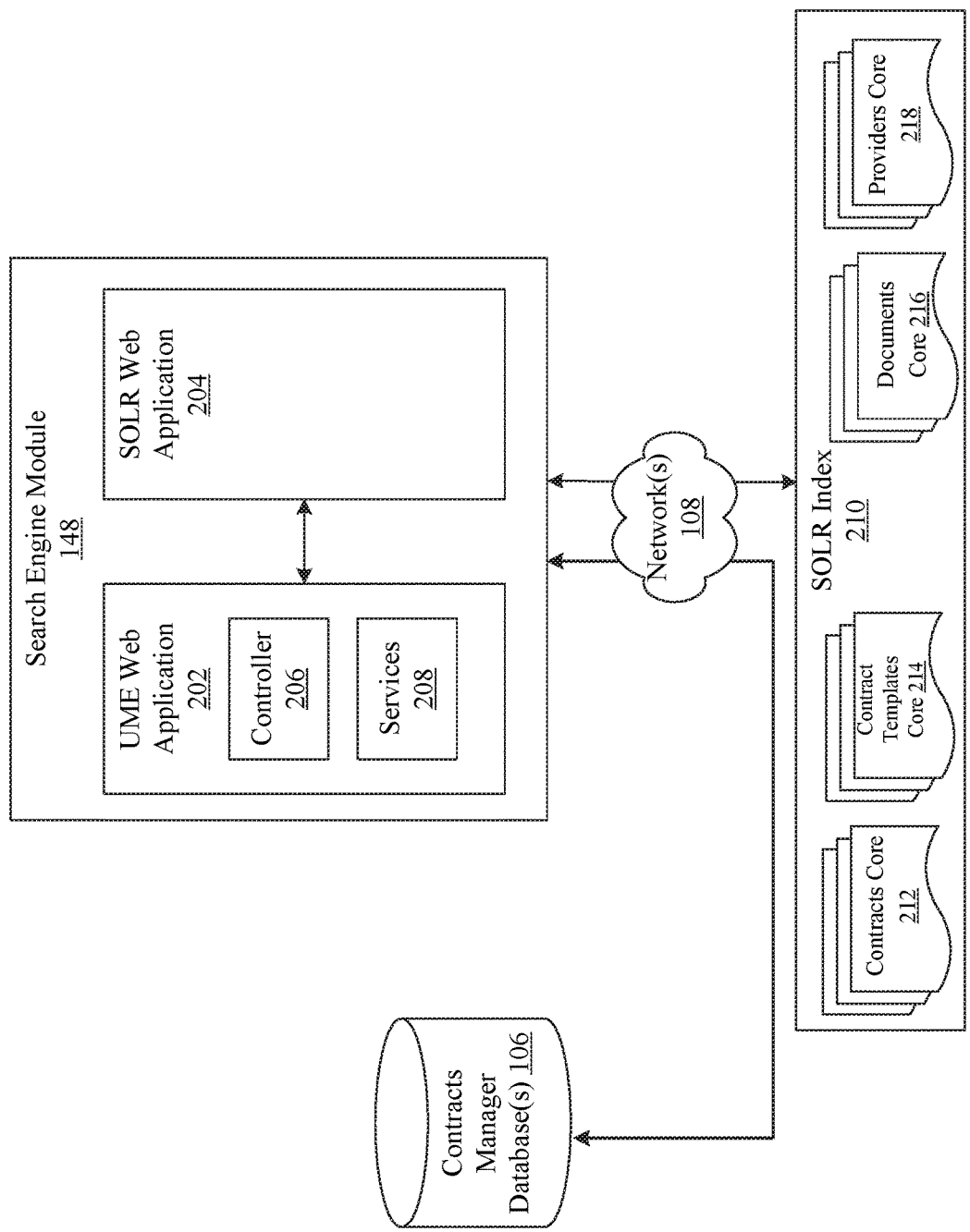
FIG. 2 is an example overview of a search engine module for the classification and indexing of contract templates based upon provider criteria, and using the provider criteria to generate a provider agreement and as part of the processing of a provider agreement request through a service provider computer according to one exemplary embodiment.

Turning to FIG. 2, FIG. 2 illustrates the search engine module 148 and will be discussed in more detail. The search engine module 148 may include, without limitation, UME web application 202 and SOLR web application 204. The UME application 202 may, in certain embodiments, include a controller 206 and a service application 208. The UME application 202 may act as a pre/post processor of search and indexing queries received from the contract manager module 140. The UME may be a loosely coupled service layer implementation that may be configured with one or more types of protocols and/or search engine technologies. For example, a search and or indexing query may, in one embodiment, be performed utilizing one or more classifier values. Classifier values may be assigned based on numerous criteria. For example, classifier(s) may be assigned to classified entities, including one or more contracting entities (e.g., contract documents, contract templates, contracts, providers, business entities (i.e., users and payer entities)) using a manual or an automated classification technique. For example a classifier value may be assigned to a region of the country (e.g., northeast, northwest, southeast, or southwest) based upon one or more zip codes. The one or more classifier values may be associated at the contract document level and may be updated and/or propagated to a corresponding contract template in real-time or near-real-time.

In certain embodiments, when performing a search to match one or more classifier values to one or more contracting entities, a simple match technique may be utilized, that is a direct match. For example, using the zip code entered by a user 124 during the input for a provider agreement request, the zip code may be matched to a specific region. The specific region may have a classifier value assigned to it such that the classifier value may be utilized during the search for corresponding contract templates and/or documents that include the same classifier value. Alternatively and/or additionally, a hierarchical match technique may be employed. In one example, the hierarchy may be composed of contract templates, where the contract templates are a compilation of one or more contract documents. However, it is to be appreciated that another hierarchy may include a more in depth search, for example, extending to one or more terms within a contract document and may utilize one or more complex search rules that support, for example, a weighted search. However, it is to be appreciated that any other matching technique may be used by the system 100.

In one example embodiment, contract entities (e.g., documents, contracts, contract templates, etc.) along with corresponding classifier values utilized during the search and/or index query process may be captured by control manager application 144 and communicated to the UME web application 202 in a JavaScript Object Notation (JSON) format. However, it is to be appreciated that other formats may be utilized to communicate the data. The captured information may be used to update SOLR index 210 and/or the contracts manager database 106 in real time or near-real time.

The UME web application may also be in communication with SOLR web application 204. The SOLR web application 204 is a main web application that may, in certain embodiments, be accessed (e.g., downloaded) by the healthcare provider computer 102 and/or the service provider computer 104 from a central repository. The SOLR web application 204 may include, in one implementation, a SOLR Home Directory, or SOLR Home folder. The SOLR Home folder may include, in one example, a main directory file, one or more configuration files, data, and/or one or more plugins. The SOLR web application 204 may be in communication with a SOLR index 210. The SOLR index 210 may include one or more cores, for example, without limitation, a contracts core 212, a contract templates core 214, a documents core 216, and/or a provider core 218. Each core may have a different configuration enabling a different behavior within that core as well as each core being able to perform one or more activities in a different fashion. For example, a contracts core 212 may update data, load data, reload data, and/or replicate data differently than a corresponding activity performed in the documents core 216.

In one example embodiment, the one or more cores of SOLR index 210 may operate in isolation of one another. For example, each core may host unrelated entities separately such that each entity does not impact another entity but maintain in communication, if necessary, via a Core Container. The use of multiple cores, such as that illustrated in SOLR index 210 may, in certain embodiments, facilitate an expedited search and/or index query (e.g., a delta index query) process. In one example embodiment, each core may include, without limitation, a configuration file and a data file. The data file may include at least a data import handler ("DIH") and one or more queries required to fetch data (e.g., documents or entities) from the contracts manager database 106 for a full index as well as for delta imports. In one example, an entity may be called a document, each document having a unique key that may be defined in an schema.xml. As discussed herein, the schema.xml may be unique to each core and may define, without limitation, the one or more fields, one or more analyzers, and one or more filters used by the core to index data and/or perform searches. For example, a contract may be a document that includes a name field, a smart identification field, a creation time, and the like. A query may be structured as, without limitation, a simple query (e.g., based on a single field), a joined query, and/or a nested query to fetch a corresponding document or contract. Inside each document, there may be multiple query types specific to a DIH. For example, a query may give data necessary to populate one or more fields of a document in a full-import. Another example query may be a delta import query. A delta import query may, for example, give data necessary to populate one or more fields while running a delta-import to update one or more documents. For example, a delta query may give one or more primary keys of a current document that may include changes since the last index time. Generally, a full index is run when a SOLR index 210 is created. After creation, delta queries are generally run based upon a last index time. A delta query may be generated automatically based upon a pre-set time. For example, a delta query may be configured to run every Sunday evening. Alternatively, a delta query may be run anytime. For example, if document changes are made as a result of legislation, a delta query may be instigated to reflect those changes.

For example, to formulate a search request, the schema.xml file may define one or more SOLR fields used by the SOLR web application 204, one or more analyzers, and/or one or more filters used by the search engine module 148 to index and/or search contract entities (e.g., documents) within the core. Therefore, data communicated to the SOLR index 210, either for search or for indexing, may communicated directly to the corresponding core. Accordingly, for example, a search of the contracts core 212 need not search through the contracts templates core 214 or the documents core 216, or the provider core 218, thereby reducing search time and reducing computational resources.

Operational Overview

Figure 3:
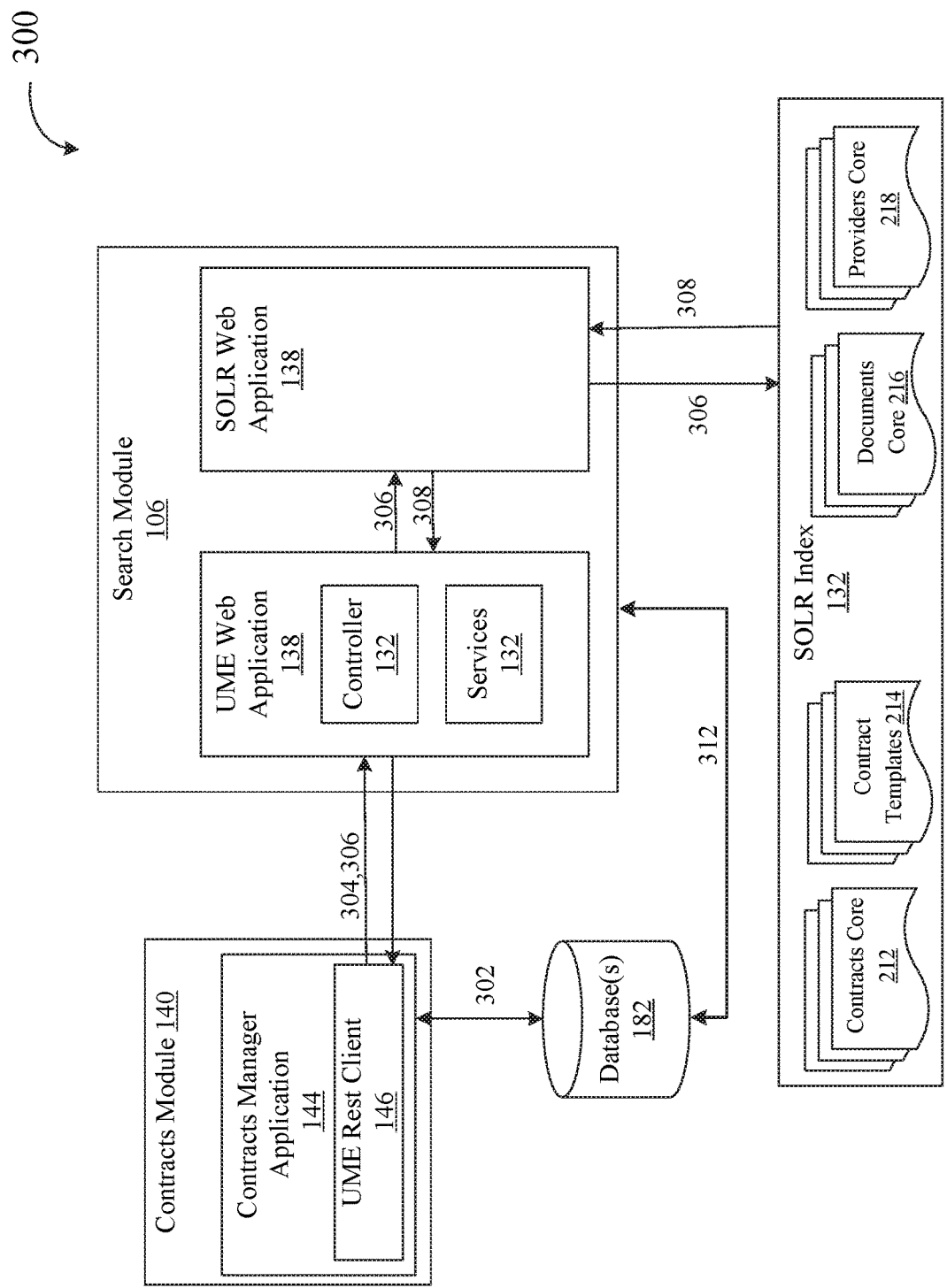
FIG. 3 is a diagram of an example data flow for the classification and indexing of contract templates based upon provider criteria, and using the provider criteria to generate a provider agreement and as part of the processing of a provider agreement request through a service provider computer according to one exemplary embodiment.
Figure 4:
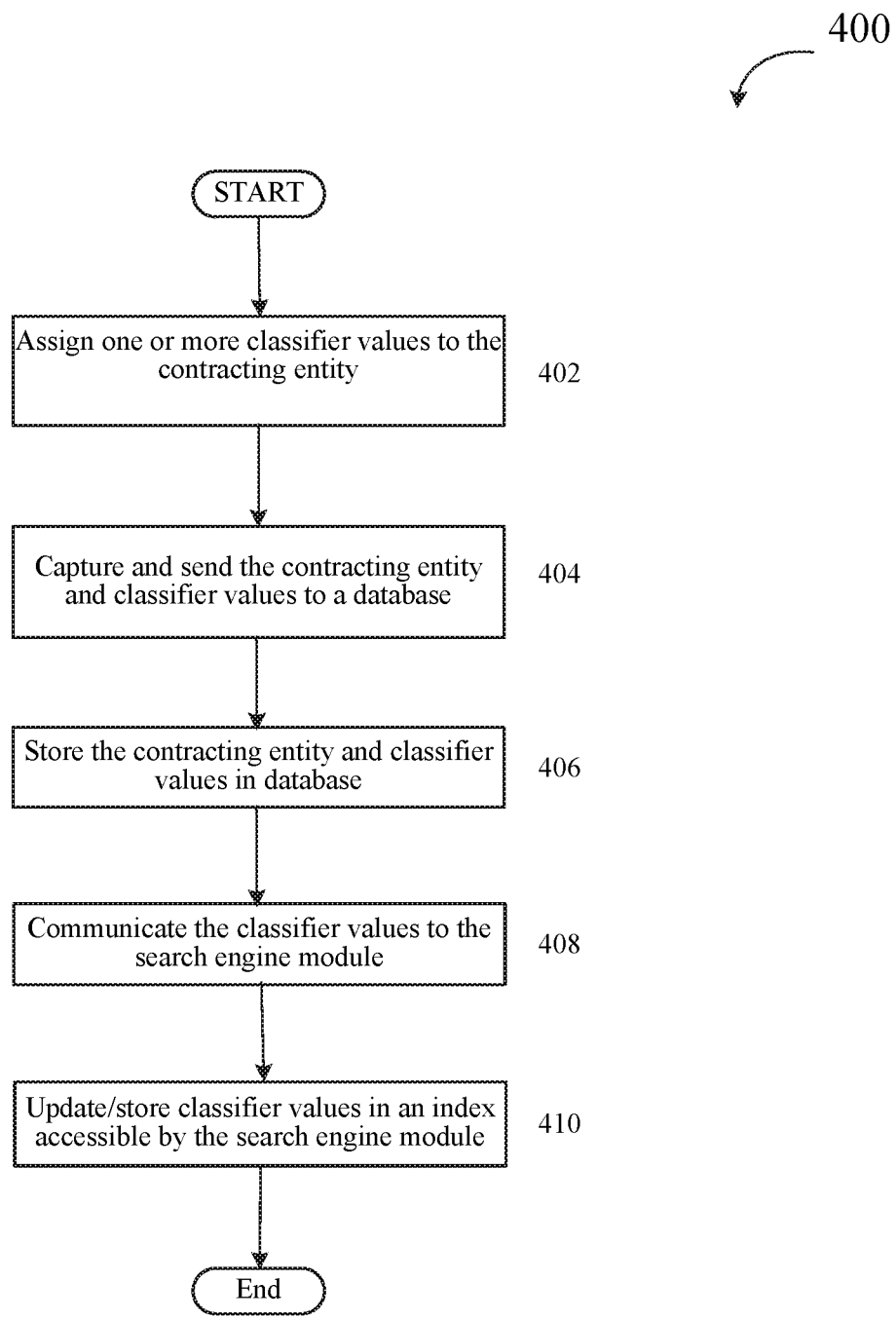
FIG. 4 is a flow chart of an example method for the classification and indexing of contract templates based upon provider criteria according to one exemplary embodiment.

FIG. 3 is a diagram of one example data flow 300 for facilitating search and/or index queries for the generation and/or the indexing of contract documents in a contract classification system, such as the system 100 including the contracts module 140 and search engine module 148 illustrated in FIG. 1. FIG. 4 is an example method for indexing a contract document based upon one or more classifier values, in accordance with one exemplary embodiment.

Referring now to FIGS. 1, 2, 3, and 4, the exemplary method 400 begins at the start step and proceeds to step 402, where one or more classifier values are assigned to a contracting entity. In one example embodiment, the contracting entities may include, without limitation, a contract document, a contract template, a contract, and/or a provider. The contract manager application 144 may capture the contracting entity. One or more classifier values may be assigned to the contracting entities using a manual and/or an automated classification technique. In one example, contract manager classifiers may include, without limitation, an agreement type classifier, a region classifier, a line of business classifier, a provider type classifier, a provider sub-type classifier, a network classifier, and/or a business entity classifier. For example, each region of the United States of America may have a classifier value. For example, the northwest region, the southwest region, the southeast region, and the northeast region may each have a unique classifier value. Each region may be associated with one or more zip codes. For example, a zip code of 99026 may be associated with the northwest region and therefore receive a classifier value corresponding to the northwest.

In step 404, the contract manager application 144 may capture the classifier information and send the contracting entity and corresponding classifier values to the contracts manager database 106 in transaction 302. In step 406, the contracts manager database 106 may store the contract entity (e.g., document, contract template, provider, etc.), along with the assigned classifier values. In one example embodiment, the contract entities may be stored according to classifier values. In yet another example embodiment, the contract entities may be stored according to contract entity type. However, it is to be appreciated that the contract entities and/or classifier values may be stored in any suitable manner for subsequent retrieval.

In one example embodiment, the contracting entity and corresponding classifier values may consist of new data. Alternatively, the contracting entity and corresponding classifier values may be an update of a contracting entity already stored in the contracts manager database 106. Where the information captured corresponds to data already stored in the contracts manager database 106, the captured information may replace the entire information already stored in the contract manager database. Alternatively, the captured information may replace only that information that differs from the information currently stored in the contracts manager database 106. In that scenario, the contract manager application 144 may determine what information differs between the two files and replace that information in the file stored in the contract manager database.

In step 408, a communication 304 may be communicated to the search engine module 148. More specifically, the contract entity and/or classifier values captured by the contracts manager application 144 may be communicated to the UME web application 202 in a JavaScript Object Notation (JSON) format. However, it is to be appreciated that other formats may be utilized to communicate the data.

In step 410, a delta index query 308 may be processed by each of the cores of the SOLR index 210. For example, without limitation, a delta import query may, for example, give data necessary to populate one or more fields while running a delta-import to update one or more documents. For example, a delta query may give one or more primary keys of a current document that may include changes since the last index time.

In step 412, one or more cores may be updated based upon one or more delta query results. The process then continues to the END step.

Figure 5:
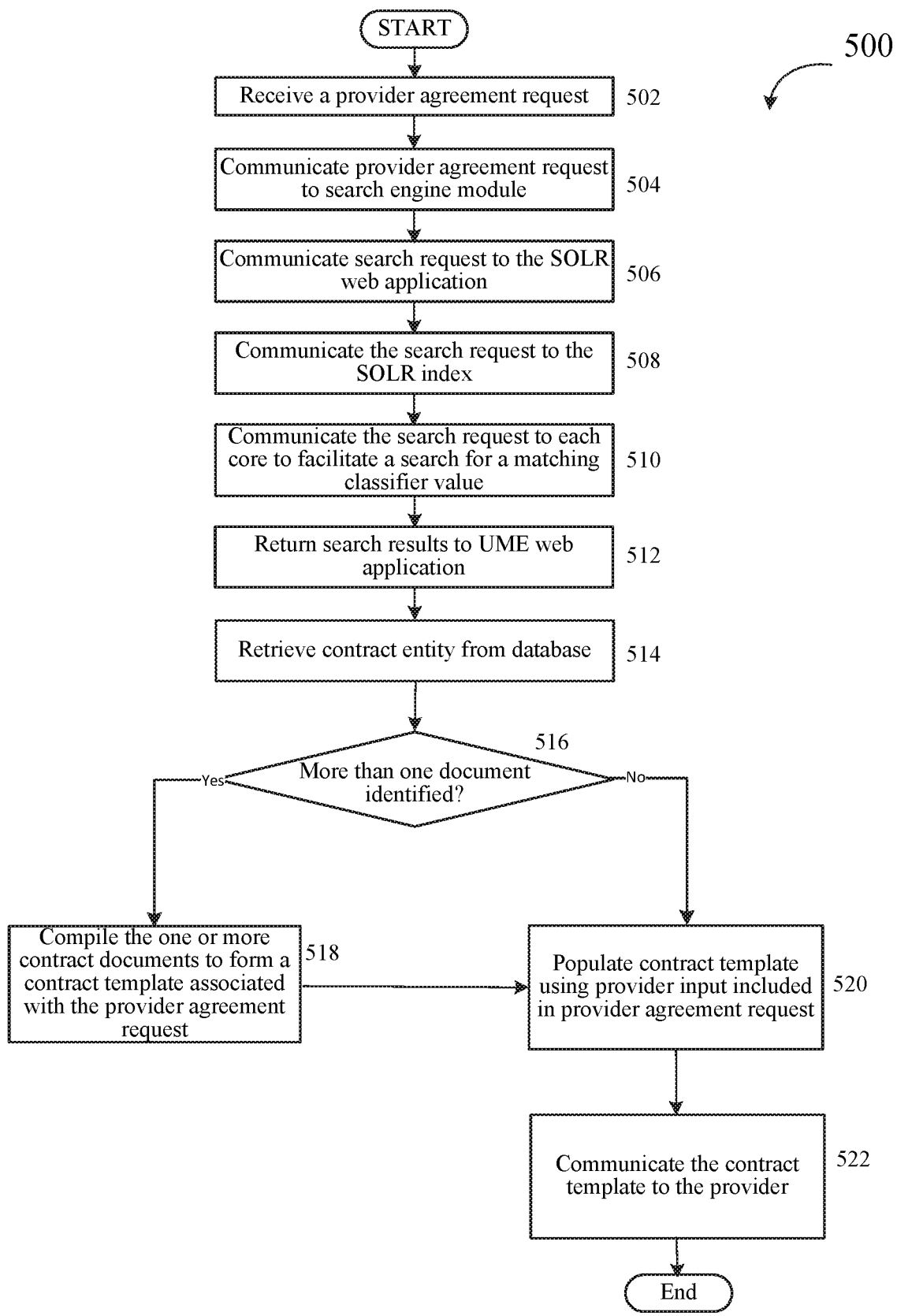
FIG. 5 is a flow chart of an example method for the generation of a provider agreement based upon provider criteria and as part of the processing of a provider agreement request through a service provider computer according to one exemplary embodiment.

FIG. 5 is an example method for querying a contract system based upon a provider agreement request submitted by a provider, such as a healthcare provider, to create a provider agreement (e.g., a contract template) corresponding to information in the provider agreement request, in accordance with one exemplary embodiment. The exemplary method 500 will be described with reference to a physician as the healthcare provider, however, this is for purpose of example as other healthcare providers could be substituted for, and should each be individually read as being a part of each of these methods. As such, where the discussion of the methods below ad the drawings state a physician, any other healthcare provider could be substituted, such as a pharmacy, a hospital, a physician's office, a clinic, a prescriber of medication, a healthcare center, or the like. In addition, the exemplary method 500 described below will be described with reference to a provider agreement request; however, this also is only for purposes of example as other requests could be substituted for the provider agreement request and each form of request should each individually be read as being used in the methods described below.

Referring now to FIGS. 1, 2, 3, and 5 the exemplary method 500 describes a method where a contract template specific to user input may be automatically generated. Method 500 begins at the start step and proceeds to step 502, where a physician may submit a provider agreement request. In one example embodiment, a physician, such as user 124 may access the search engine module 148 through the contract manager application 144. The contract manager application 144 may prompt the user to enter pertinent contracting information. For example, the contract manager application 144 may prompt the user to fill in one or more fields, such as provider name(s), address(es), TIN, provider identification (e.g., NPI), type of care provided (e.g., neurologist, primary care, pediatrics, OBGYN, etc.), etc. By way of another example, the contract manager application 144 may provide one or more drop down boxes, providing the user with options from which to select the corresponding information. Alternatively, the search engine module 148 may receive the provider information from the data files 118 associated with the healthcare provider computer 102. The search engine module 148 may "pull" the provider information from the healthcare provider computer or the healthcare provider computer may "push" the provider information to the search engine module 148.

The information submitted by the user may, in one non-limiting example, correspond to a classifier value. For example, the one or more fields containing the user input and/or selection may correspond to one or more classifiers, for example, without limitation, an agreement type classifier, a region classifier, a line of business classifier (e.g., Medicare, Preferred Provider Organization ("PPO"), health maintenance organization ("HMO"), etc.), a provider type classifier, a provider sub-type classifier, a network classifier, and/or a business entity classifier In step 504, the contract manager application 144 may communicate the classifier values to the UME application 202 in a search request 306. In one example, the communication is a Hypertext Transfer Protocol (HTTP) communication however; it is to be appreciated that other communication protocols may be used. The HTTP communication between the contracts manager application 144 and the UME web application 202 may be transmitted using the UME REST client 146. In one example, the UME REST client 146 may be an Application Programming Interface exposed by the UME web application 202 to enable access by the UME web application to the contracts manager application 144. The loosely coupled components provide for an implementation that may, in certain embodiments, be integrated with one or more types of protocols and/or integrated with the contracts manager application 144.

In step 506, the UME web application may communicate the search request 306 to the SOLR web application 204. In step 508, the SOLR web application 204 may transmit the search request 306 to SOLR index 132, and in step 510 the SOLR index 132 may communicate the search request 306 to one or more cores. Each core, using the schema.xml unique to that core, may perform a search specific to the corresponding core.

The SOLR index may facilitate the search of each of the one or more cores contained within the SOLR index 132 for a classifier value match. In one example, the SOLR index 132 may search a contracts core 212, a contract templates core 214, a documents core 216, and a provider core 218. The match may be a simple match, for example, where the classifier value corresponding to the user input matches a classifier value associated with a contracting entity (e.g., a document, a contract, a contract template, a provider, etc.). For example, when a business address is submitted by the user in the initial provider agreement request 304, the zip code may correspond to a classifier value corresponding to the northwest, each of the cores within the SOLR index 132 may be searched for contract entities that include a matching classifier value. Alternatively, the match may be a hierarchical match, where a natural hierarchy of one or more contracting entities is taken into account. Furthermore, a match may, in certain embodiments, extend to terms and/or fields within the contract document.

In step 512, one or more search query results may be communicated via a search results response 308 to the UME web application 202 and/or the SOLR web application 204. In one example embodiment, the search results response 308 may include a key. A key may be a link to one or more contract entities stored in a database, such as the contracts manager database 106. In one non-limiting example, the key may correspond to an entity identifier. For example, the classifier value associated with the northwest region may have matched a classifier value attached to a key stored in the documents core 216.

At step 514, one or more contract entities may be retrieved from a database, such as contracts manager database 106. In step 516, an inquiry is conducted to determine whether one or more keys were communicated in search results response 308. If the search engine module 148 determines that multiple keys were identified, the YES branch is followed to step 518, and if the search engine module 148 determines that only one key was identified during the search using the information provided in the provider agreement request 306, the NO branch is followed to step 520.

In step 518, the one or more contract entities may be compiled to form a contract template. The contract template may include, without limitation multiple contract entities, including, a contract document, a contract template, a contract, and/or a provider. In step 520, one or more fields of the contract template may be populated using the information submitted by the user 124 in the provider agreement request 306. In step 522, the provider may communicate a completed contract template to the healthcare provider computer 102 via the contract manager application 144 for approval. The process then continues to the END step.

The methods described and shown in FIGS. 4 and 5 may be carried out or performed in any suitable order as desired in various embodiments. Additionally, in certain exemplary embodiments, at least a portion of the operations may be carried out in parallel. Furthermore, in certain exemplary embodiments, less than or more than the operations described in FIGS. 4 and 5 may be performed.

Likewise, while FIGS. 4 and 5 have been described primarily in conjunction with FIG. 3, it will be appreciated that variations of FIG. 3 are available. While certain example embodiments disclosed herein describes the search engine module 148 as being separate of the service provider computer 104, in alternate embodiments, the search engine module 148 or the functions that it completes may be part of the service provider computer 104. In those embodiments where the search engine module is incorporated into the service provider computer 104, and with regard to the methods described above, the elements describing transmitting or receiving between the service provider computer 104 and the search engine module 148 may be internal transmissions within the service provider computer 104 or may be omitted altogether. The intent being that, in alternate embodiments, any of the devices/computers discussed in FIGS. 1 and 2 are capable of completing all or any part of the methods described with reference to FIGS. 3-5.

Accordingly, example embodiments disclosed herein can provide the technical effects of creating a system and method supporting the classification and indexing of contract documentation and templates for identification based upon provider criteria utilized to automate the generation of a provider agreement. In this regard, health plans may be created, offered, and executed without user intervention, thereby reducing the risk of human error.

Although example embodiments of the disclosure have been described, one of ordinary skill in the art will recognize that numerous other modifications and alternative embodiments are within the scope of the disclosure. For example, any other device or component that is properly configured may perform any of the functionality and/or processing capabilities described with respect to a particular device or component. Furthermore, while various example implementations and architectures have been described in accordance with example embodiments of the disclosure, one of ordinary skill in the art will appreciate that numerous other modifications to the example implementations and architectures described herein are also within the scope of this disclosure.

Certain aspects of the disclosure are described above with reference to block and flow diagrams of systems, methods, apparatuses, and/or computer program products according to example embodiments. It will be understood that one or more blocks of the block diagrams and steps of the flow diagrams, and combinations of blocks in the block diagrams and steps of the flow diagrams, respectively, may be implemented by execution of computer-executable program instructions. Likewise, some blocks of the block diagrams and steps of the flow diagrams may not necessarily need to be performed in the order presented, or may not necessarily need to be performed at all, according to some embodiments. Further, additional components and/or operations beyond those depicted in blocks of the block and/or steps of the flow diagrams may be present in certain embodiments.

Accordingly, blocks of the block diagrams and steps of the flow diagrams support combinations of means for performing the specified functions, combinations of elements or steps for performing the specified functions and program instruction means for performing the specified functions. It will also be understood that each block of the block diagrams and step of the flow diagrams, and combinations of blocks in the block diagrams and steps of the flow diagrams, are implemented by special-purpose, hardware-based computer systems that perform the specified functions, elements or steps, or combinations of special-purpose hardware and computer instructions.

Computer-executable program instructions may be loaded onto a special-purpose computer or other particular machine, a processor, or other programmable data processing apparatus to produce a special-purpose machine, such that execution of the instructions on the computer, processor, or other programmable data processing apparatus causes one or more functions or steps specified in the flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or steps specified in the flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium which can be used to store the information and which can be accessed. Combinations of any of the above are also included within the scope of CRSM. Alternatively, computer-readable communication media (CRCM) may include computer-readable instructions, program modules, or other data transmitted within a data signal, such as a carrier wave, or other transmission. However, as used herein, CRSM does not include CRCM.

Although example embodiments have been described in language specific to structural features and/or methodological acts, it is to be understood that the disclosure is not necessarily limited to the specific features or acts described. Rather, the specific features and acts are disclosed as illustrative forms of implementing the example embodiments. Conditional language, such as, among others, "can," "could," "might," or "may," unless specifically stated otherwise, or otherwise understood within the context as used, is generally intended to convey that certain example embodiments could include, while other example embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

What is claimed is:

1. A system, comprising;
   at least one memory operable to store computer-executable instructions; and
   at least one processor configured to access the at least one memory and execute the computer-executable instructions to:
   receive, from a provider computer for a provider, a provider agreement request, wherein the provider agreement request comprises provider input corresponding to one or more classifier values;
   for each core of a plurality of cores, searching the core to determine an indexed classifier value that matches the one or more classifier values, wherein each core of the plurality of cores performs the search using a schema that is unique to the core, and further wherein the indexed classifier value comprises at least one key corresponding to one or more contract entities stored in a contract database, wherein each schema comprises a plurality of fields used to index and search contract entities for the core associated with the schema, and wherein each core of the plurality of cores is isolated from the other cores of the plurality of cores, and each core of the plurality of cores comprises a configuration file and a data file;
   for each determined index classifier value, identify, based upon the at least one key of the determined index classifier value, a contract entity stored in a contract database;
   for each identified contract entity, access the identified contract entity stored in the contract database;
   compile each identified contract entity into a contract template;

access the received provider input associated with the provider agreement request;

pre-populate one or more fields of the contract template with the provider input; and communicate the contract template to the provider computer for a signature from the provider.

2. The system of claim 1, wherein each core of the plurality of cores is isolated from the other cores of the plurality of cores, and each core of the plurality of cores is searched in parallel.

3. The system of claim 1, wherein the data file for a core comprises a data import handler and one or more queries used to fetch data from the contracts database.

4. The system of claim 1, wherein the processor configured to search the core to determine an indexed classifier value that matches the one or more classifier values further comprises the processor configured to formulate a query including the one or more classifier values using the schema that is unique to the core.

5. The system of claim 1, wherein the indexed classifier value that matches the one or more classifier values is a simple match or a hierarchical match.

6. The system of claim 1, wherein each core of the plurality of cores comprises at least one of a contracts core, a contract template core, a document core, or a provider core.

7. The system of claim 1, wherein the one or more classifier values comprises at least one of an agreement type classifier, a region classifier, a line of business classifier, a provider type classifier, a provider sub-type classifier, a network classifier, or a business entity classifier.

8. The system of claim 1, wherein the contract entities comprises at least one of a contract document, a contract template, a contract, a provider, a payer, or a business entity.

9. The system of claim 1, wherein the provider input includes at least one of a provider name, a provider service address, a provider billing address, a provider tax identification number, or a provider identification number.

10. The system of claim 1, wherein the one or more classifier values are associated at a contract document level and are updated or propagated to the contracts database or the one or more cores in real time or near-real time.

11. A computer-implemented method for automatically generating a provider agreement, comprising:

receiving by a service provider computer associated with a service provider and comprising one or more computer processors from a provider computer for a provider, a provider agreement request, wherein the provider agreement request comprises provider input corresponding to one or more classifier values;

for each core of a plurality of cores, searching, by the service provider computer, the core to determine an indexed classifier value that matches the one or more classifier values, wherein each core of the plurality of cores performs the search using a schema that is unique to the core, and further wherein the indexed classifier value comprises at least one key corresponding to one or more contract entities stored in a contract database, wherein each schema comprises a plurality of fields used to index and search contract entities for the core associated with the schema, and wherein each core of the plurality of cores is isolated from the other cores of the plurality of cores, and each core of the plurality of cores comprises a configuration file and a data file;

for each determined index classifier value, identifying, by the service provider computer, based upon the at least one key of the determined index classifier value, a contract entity stored in a contract database;

for each identified contract entity, accessing, by the service provider computer, the identified contract entity stored in the contract database;

compiling, by the service provider computer, each identified contract entity into a contract template;

accessing, by the service provider computer, the received provider input associated with the provider agreement request;

pre-populating, by the service provider computer, one or more fields of the contract template with the provider input; and communicating, by the service provider computer, the contract template to the provider computer for a signature from the provider.

12. The computer-implemented method of claim 11, wherein each core of the plurality of cores is isolated from the other cores of the plurality of cores, and each core of the plurality of cores is searched in parallel.

13. The computer-implemented method of claim 11, wherein the data file for a core comprises a data import handler and one or more queries used to fetch data from the contracts database.

14. The computer-implemented method of claim 11, wherein searching the core to determine an indexed classifier value that matches the one or more classifier values further comprises:

formulating, by the service provider computer, a query including the one or more classifier values using the schema that is unique to the core.

15. The computer-implemented method of claim 11, wherein the indexed classifier value that matches the one or more classifier values is a simple match or a hierarchical match.

16. The computer-implemented method of claim 11, wherein each core of the plurality of cores comprises at least one of a contracts core, a contract template core, a document core, or a provider core.

17. The computer-implemented method of claim 11, wherein the one or more classifier values comprises at least one of an agreement type classifier, a region classifier, a line of business classifier, a provider type classifier, a provider sub-type classifier, a network classifier, or a business entity classifier.

18. The computer-implemented method of claim 11, wherein the contract entities comprises at least one of a contract document, a contract template, a contract, a provider, a payer, or a business entity.

19. The computer-implemented method of claim 11, wherein the provider input includes at least one of a provider name, a provider service address, a provider billing address, a provider tax identification number, or a provider identification number.

20. The computer-implemented method of claim 19, wherein the one or more classifier values are associated at a contract document level and are updated or propagated to the contracts database or the one or more cores in real time or near-real time.

* * * * *